United States Patent
Soya et al.

(10) Patent No.: US 12,049,566 B2
(45) Date of Patent: Jul. 30, 2024

(54) METHOD FOR PRESERVING LEUCO CHROMOGEN-CONTAINING AQUEOUS SOLUTION

(71) Applicant: HITACHI CHEMICAL DIAGNOSTICS SYSTEMS CO., LTD., Tokyo (JP)

(72) Inventors: Haruyo Soya, Sunto-gun (JP); Yuki Katayama, Sunto-gun (JP)

(73) Assignee: HITACHI CHEMICAL DIAGNOSTICS SYSTEMS CO., LTD., Tokyo (JP)

( * ) Notice: Subject to any disclaimer, the term of this patent is extended or adjusted under 35 U.S.C. 154(b) by 1590 days.

(21) Appl. No.: 16/320,343

(22) PCT Filed: Jul. 28, 2017

(86) PCT No.: PCT/JP2017/027439
§ 371 (c)(1),
(2) Date: Jan. 24, 2019

(87) PCT Pub. No.: WO2018/021529
PCT Pub. Date: Feb. 1, 2018

(65) Prior Publication Data
US 2019/0177548 A1 Jun. 13, 2019

(30) Foreign Application Priority Data

Jul. 29, 2016 (JP) ................................. 2016-150499

(51) Int. Cl.
| | | |
|---|---|---|
| C09B 67/14 | (2006.01) | |
| C09B 21/00 | (2006.01) | |
| C09B 67/00 | (2006.01) | |
| C09B 67/44 | (2006.01) | |
| C12Q 1/28 | (2006.01) | |

(52) U.S. Cl.
CPC .......... C09B 67/0017 (2013.01); C09B 21/00 (2013.01); C09B 67/00 (2013.01); C09B 67/0083 (2013.01); C12Q 1/28 (2013.01)

(58) Field of Classification Search
CPC .. C09B 67/0017; C09B 21/00; C09B 67/0083
See application file for complete search history.

(56) References Cited

U.S. PATENT DOCUMENTS

| | | | | |
|---|---|---|---|---|
| 3,627,697 A | * | 12/1971 | Rey ......................... | C12Q 1/54 435/14 |
| 4,851,353 A | * | 7/1989 | Miike ....................... | C12Q 1/28 436/66 |
| 5,041,636 A | * | 8/1991 | Sakata ..................... | C12Q 1/62 562/439 |
| 6,743,597 B1 | * | 6/2004 | Guo ......................... | C12Q 1/28 435/14 |
| 7,354,732 B2 | * | 4/2008 | Yonehara ................. | C12Q 1/28 435/28 |
| 2007/0026523 A1 | * | 2/2007 | Taniguchi ................ | C12Q 1/37 436/18 |
| 2007/0224685 A1 | | 9/2007 | Kouzuma et al. | |
| 2008/0241816 A1 | | 10/2008 | Taniguchi et al. | |
| 2008/0295259 A1 | | 12/2008 | Ueda et al. | |
| 2009/0053823 A1 | | 2/2009 | Yonehara et al. | |
| 2011/0015391 A1 | | 1/2011 | Yonehara et al. | |
| 2013/0123491 A1 | | 5/2013 | Soya et al. | |
| 2013/0252343 A1 | | 9/2013 | Soya | |

FOREIGN PATENT DOCUMENTS

| | | |
|---|---|---|
| EP | 1 260 498 | 11/2002 |
| EP | 2653551 A1 | 10/2013 |
| JP | 57-029297 | 2/1982 |
| JP | 62-093261 | 4/1987 |
| JP | 03-206896 | 9/1991 |
| JP | 06-289015 | 10/1994 |
| JP | 09-019296 | 1/1997 |
| JP | 2002-144746 | 5/2002 |
| JP | 2006-087356 | 4/2006 |
| JP | 2006-152186 | 6/2006 |
| JP | 2008-201968 | 9/2008 |

(Continued)

OTHER PUBLICATIONS

Reljic; Clin. Chem. 1992, 38, 522-525. https://doi.org/10.1093/clinchem/38.4.522 (Year: 1992).*
Aoyama, Journal of Clinical Laboratory Medicine vol. 41, No. 9 (1997) 1014-19.
Supplementary Partial European Search Report issued Aug. 13, 2020 in counterpart application EP 17834531.0. (16 pages).
International Search Report (Oct. 31, 2017).
Extended European Search Report issued in corresponding European Patent Application No. 17834531.0 dated Nov. 13, 2020.

*Primary Examiner* — Daniel R Carcanague
(74) *Attorney, Agent, or Firm* — Morgan, Lewis & Bockius LLP

(57) ABSTRACT

The present invention provides a method for preserving a leuco chromogen-containing aqueous solution comprising: adding at least one acid compound selected from the group consisting of a phosphoric acid compound, a carboxylic acid compound, a sulfonic acid compound, and a sulfuric acid compound to a leuco chromogen-containing aqueous solution; a method for stabilizing a leuco chromogen in an aqueous solution comprising: adding at least one acid compound selected from the group consisting of a phosphoric acid compound, a carboxylic acid compound, a sulfonic acid compound, and a sulfuric acid compound to a leuco chromogen-containing aqueous solution; and a liquid reagent comprising a leuco chromogen and at least one acid compound selected from the group consisting of a phosphoric acid compound, a carboxylic acid compound, a sulfonic acid compound, and a sulfuric acid compound.

20 Claims, No Drawings

(56) References Cited

FOREIGN PATENT DOCUMENTS

| | | |
|---|---|---|
| JP | 2009183203 A | 8/2009 |
| JP | 2011-026359 | 2/2011 |
| JP | 2012-024014 | 2/2012 |
| JP | 5274590 B2 | 8/2013 |
| WO | 2005/088305 | 9/2005 |
| WO | 2005087946 A1 | 9/2005 |
| WO | 2006/013921 | 2/2006 |
| WO | 2007/083703 | 7/2007 |
| WO | 2009/069310 | 6/2009 |
| WO | 2009/116575 | 9/2009 |
| WO | 2012/020746 | 2/2012 |
| WO | 2012/081540 | 6/2012 |
| WO | 2013/118744 | 8/2013 |
| WO | 2014/088056 | 6/2014 |

\* cited by examiner

METHOD FOR PRESERVING LEUCO CHROMOGEN-CONTAINING AQUEOUS SOLUTION

TECHNICAL FIELD

The present invention relates to a method for preserving a leuco chromogen-containing aqueous solution, a method for stabilizing a leuco chromogen in an aqueous solution, and a liquid reagent comprising a leuco chromogen.

This application is the national phase of PCT Application No. PCT/JP2017/027439 filed Jul. 28, 2017, which in turn claims priority on Japanese Patent Application No. 2016-150499, filed on Jul. 29, 2016, the content of which are incorporated herein by reference.

BACKGROUND ART

A leuco chromogen is a chromogen that reacts with hydrogen peroxide in the presence of a peroxidative substance such as peroxidase to produce a dye, and is a chromogen that produces a dye by itself unlike a coupling-type chromogen, and as examples thereof, a phenothiazine leuco chromogen, a triphenylmethane leuco chromogen, and a diphenylamine leuco chromogen have been known (see e.g., Patent Documents 1 to 3).

As in the coupling-type chromogen, the leuco chromogen is often used for quantification of components to be quantified such as cholesterol and glycated hemoglobin present in a sample such as serum. Specifically, clinical laboratory examination often involve: converting the components to be quantified in the sample into hydrogen peroxide; reacting the produced hydrogen peroxide with a leuco chromogen in the presence of a peroxidative substance such as peroxidase to produce a dye; and determining the components to be quantified in the sample based on absorbance of the produced dye. In particular, the leuco chromogen is suitably used as a highly sensitive chromogen for the quantification of the components to be quantified present in only a trace amount in the sample (see e.g., Non-Patent Document 1).

In this way, the leuco chromogen is used as a highly sensitive chromogen for quantifying a trace amount of the components to be quantified in a sample, whereas there is a disadvantage that the preservation stability thereof is poor, and particularly, spontaneous color development occurs in a solution by light irradiation such as room lighting. In order to solve the problem of poor stability of this leuco chromogen, various methods for stabilizing leuco chromogens in a solution have been reported (see, e.g., Patent Document 4 to 9).

PRIOR ART DOCUMENTS

Patent Documents
 [Patent Document 1] Japanese Unexamined Patent Application Publication No. S57-029297
 [Patent Document 2] Japanese Unexamined Patent Application Publication No. H3-206896
 [Patent Document 3] Japanese Unexamined Patent Application Publication No. S62-093261
 [Patent Document 4] PCT International Publication No. WO 2005/088305
 [Patent Document 5] PCT International Publication No. WO 2007/083703
 [Patent Document 6] PCT International Publication No. WO 2012/020746
 [Patent Document 7] PCT International Publication No. WO 2012/081540
 [Patent Document 8] PCT International Publication No. WO 2013/118744
 [Patent Document 9] PCT International Publication No. WO 2014/088056

Non-Patent Documents
 [Non-Patent Document 1] Journal of Clinical Laboratory Medicine, 1997, Vol. 41, No. 9, p. 1014-1019

SUMMARY OF INVENTION

Problems to be Solved by the Invention

An object of the present invention is to provide a method for preserving a leuco chromogen-containing aqueous solution, a method for stabilizing a leuco chromogen in an aqueous solution, whereby the leuco chromogen can be preserved stably in an aqueous solution, and a liquid reagent for stably preserving the leuco chromogen.

Means for Solving the Problems

The inventors of the present invention conducted extensive studies in order to solve this problem, and consequently found that a leuco chromogen is stably preserved in an aqueous solution by adding at least one acid compound selected from the group consisting of a phosphoric acid compound, a carboxylic acid compound, a sulfonic acid compound, and a sulfuric acid compound to a leuco chromogen-containing aqueous solution to complete the present invention thereby.

Specifically, the present invention relates to the following [1] to [21].

[1] A method for preserving a leuco chromogen-containing aqueous solution comprising: adding at least one acid compound selected from the group consisting of a phosphoric acid compound, a carboxylic acid compound, a sulfonic acid compound, and a sulfuric acid compound to a leuco chromogen-containing aqueous solution.

[2] The method according to [1], wherein the phosphoric acid compound is a compound selected from the group consisting of phosphoric acid, alkyl phosphoric acid, polyoxyethylene alkyl ether phosphoric acid, polyoxyethylene polycyclic phenyl ether phosphoric acid, and salts thereof.

[3] The method according to [1] or [2], wherein the carboxylic acid compound is a compound selected from the group consisting of polyoxyethylene alkyl ether fatty acid, N-acylamino acid in which a hydrogen atom of the amino group may be substituted with a substituent, and salts thereof.

[4] The method according to any one of [1] to [3], wherein the sulfonic acid compound is a compound selected from the group consisting of N-acyl taurine in which a hydrogen atom of the amino group may be substituted with a substituent, α-olefin sulfonic acid, alkyl sulfocarboxylic acid, polyoxyethylene alkyl sulfocarboxylic acid, and salts thereof.

[5] The method according to any one of [1] to [4], wherein the sulfuric acid compound is a compound selected from the group consisting of alkyl sulfuric acid, polyoxyethylene alkyl ether sulfuric acid, and salts thereof.

[6] The method according to any one of [1] to [5], wherein the leuco chromogen is a phenothiazine chromogen.

[7] The method according to [6], wherein the phenothiazine chromogen is 10-(carboxymethylaminocarbonyl)-3,7-bis(dimethylamino)phenothiazine or a salt thereof.

[8] A method for stabilizing a leuco chromogen in an aqueous solution comprising: adding at least one acid compound selected from the group consisting of a phosphoric acid compound, a carboxylic acid compound, a sulfonic acid compound, and a sulfuric acid compound to a leuco chromogen-containing aqueous solution.

[9] The method according to [8], wherein the phosphoric acid compound is a compound selected from the group consisting of phosphoric acid, alkyl phosphoric acid, polyoxyethylene alkyl ether phosphoric acid, polyoxyethylene polycyclic phenyl ether phosphoric acid, and salts thereof.

[10] The method according to [8] or [9], wherein the carboxylic acid compound is a compound selected from the group consisting of polyoxyethylene alkyl ether fatty acid, N-acylamino acid in which a hydrogen atom of the amino group may be substituted with a substituent, and salts thereof.

[11] The method according to any one of [8] to [10], wherein the sulfonic acid compound is a compound selected from the group consisting of N-acyl taurine in which a hydrogen atom of the amino group may be substituted with a substituent, α-olefin sulfonic acid, alkyl sulfocarboxylic acid, polyoxyethylene alkyl sulfocarboxylic acid, and salts thereof.

[12] The method according to any one of [8] to [11], wherein the sulfuric acid compound is a compound selected from the group consisting of alkyl sulfuric acid, polyoxyethylene alkyl ether sulfuric acid, and salts thereof.

[13] The method according to any one of [8] to [12], wherein the leuco chromogen is a phenothiazine chromogen.

[14] The method according to [13], wherein the phenothiazine chromogen is 10-(carboxymethylaminocarbonyl)-3,7-bis(dimethylamino)phenothiazine or a salt thereof.

[15] A liquid reagent comprising a leuco chromogen and at least one acid compound selected from the group consisting of a phosphoric acid compound, a carboxylic acid compound, a sulfonic acid compound, and a sulfuric acid compound.

[16] The reagent according to [15], wherein the phosphoric acid compound is a compound selected from the group consisting of phosphoric acid, alkyl phosphoric acid, polyoxyethylene alkyl ether phosphoric acid, polyoxyethylene polycyclic phenyl ether phosphoric acid, and salts thereof.

[17] The reagent according to [15] or [16], wherein the carboxylic acid compound is a compound selected from the group consisting of polyoxyethylene alkyl ether fatty acid, N-acylamino acid in which a hydrogen atom of the amino group may be substituted with a substituent, and salts thereof.

[18] The reagent according to any one of [15] to [17], wherein the sulfonic acid compound is a compound selected from the group consisting of N-acyl taurine in which a hydrogen atom of the amino group may be substituted with a substituent, α-olefin sulfonic acid, alkyl sulfocarboxylic acid, polyoxyethylene alkyl sulfocarboxylic acid, and salts thereof.

[19] The reagent according to any one of [15] to [18], wherein the sulfuric acid compound is a compound selected from the group consisting of alkyl sulfuric acid, polyoxyethylene alkyl ether sulfuric acid, and salts thereof.

[20] The reagent according to any one of [15] to [19], wherein the leuco chromogen is a phenothiazine chromogen.

[21] The reagent according to [20], wherein the phenothiazine chromogen is 10-(carboxymethylaminocarbonyl)-3,7-bis(dimethylamino)phenothiazine or a salt thereof.

Effects of the Invention

The present invention provides a method for preserving a leuco chromogen-containing aqueous solution and a method for stabilizing a leuco chromogen in an aqueous solution, whereby the leuco chromogen can be stably preserved in an aqueous solution, and a liquid reagent comprising a leuco chromogen.

Mode for Carrying Out the Invention (1) Method for Preserving Leuco Chromogen-Containing Aqueous Solution and Method for Stabilizing Leuco Chromogen in Aqueous Solution The present invention relates to a method for preserving a leuco chromogen-containing aqueous solution. According to the method for preserving a leuco chromogen-containing aqueous solution of the present invention, a leuco chromogen is stably preserved in an aqueous solution.

In the present invention, the leuco chromogen means a substance that is converted into a dye by itself in the presence of hydrogen peroxide and a peroxidative substance. Examples of the peroxidative substance include peroxidase.

In the present invention, the phrase "the leuco chromogen is stably preserved in the aqueous solution" means that the leuco chromogen in the aqueous solution is stable against heat, or stable against light, and it is preferable that the leuco chromogen is stable against the light in the aqueous solution. In the method for preserving a leuco chromogen-containing aqueous solution of the present invention, at least one acid compound selected from the group consisting of a phosphoric acid compound, a carboxylic acid compound, a sulfonic acid compound, and a sulfuric acid compound is added to the leuco chromogen-containing aqueous solution.

The phosphoric acid compound in the present invention is not particularly as long as it is a compound having a phosphoric acid group ($PO_4$) or a salt thereof, and examples thereof include phosphoric acid or a salt thereof, alkyl phosphoric acid or a salt thereof, polyoxyethylene alkyl ether phosphoric acid or a salt thereof, and polyoxyethylene polycyclic phenyl ether phosphoric acid or a salt thereof.

Examples of the salt include a lithium salt, a sodium salt, a potassium salt, an ammonium salt, a magnesium salt, a calcium salt, and a monoethanolamine salt.

Examples of the alkyl in alkyl phosphoric acid and polyoxyethylene alkyl ether phosphoric acid include alkyl having 8 to 20 carbon atoms, and alkyl having 10 to 18 carbon atoms is preferable.

Examples of the alkyl having 8 to 20 carbon atoms include octyl, nonyl, decyl, undecyl, dodecyl (lauryl), tridecyl, tetradecyl (myristyl), pentadecyl, hexadecyl (cetyl), heptadecyl, octadecyl (stearyl), oleyl, nonadecyl, and icosyl. Examples of the alkyl having 10 to 18 carbon atoms include decyl, undecyl, dodecyl (lauryl), tridecyl, tetradecyl (myristyl), pentadecyl, hexadecyl (cetyl), heptadecyl, octadecyl (stearyl), and oleyl.

Examples of polycyclic phenyl in the polyoxyethylene polycyclic phenyl ether phosphoric acid include a phenyl group substituted by two or more groups (substituents) having one aromatic ring in the group, and a phenyl group substituted with one or more groups (substituents) having two or more aromatic rings in the group. Examples of the group having one aromatic ring in the group include benzyl, and 1-(phenyl)ethyl. Examples of the group having two or more aromatic rings in the group include naphthyl.

Specific examples of the phosphoric acid compound include phosphoric acid, sodium phosphate, potassium phosphate, sodium monohydrogen phosphate, sodium dihydrogen phosphate, potassium monohydrogen phosphate, potassium dihydrogen phosphate, NIKKOL SLP-N [alkyl phosphoric acid salt (sodium lauryl phosphate); manufactured by Nikko Chemicals Co., Ltd.)], PLYSURF A212C [polyoxyethylene alkyl ether phosphoric acid (polyoxyethylene tridecyl ether phosphoric acid); manufactured by DKS Co. Ltd.], PLYSURF A215C [polyoxyethylene alkyl ether phosphoric acid (polyoxyethylene tridecyl ether phosphoric acid); manufactured by DKS Co. Ltd.], PLYSURF A208F [polyoxyethylene alkyl ether phosphoric acid (polyoxyethylene octyl ether phosphoric acid); manufactured by DKS Co. Ltd.], PLYSURF A219B [polyoxyethylene alkyl ether phosphoric acid (polyoxyethylene lauryl ether phosphoric acid); manufactured by DKS Co. Ltd.], PLYSURF DB-01 [polyoxyethylene alkyl ether phosphoric acid salt (polyoxyethylene lauryl ether phosphate-monoethanolamine salt); manufactured by DKS Co. Ltd.], and PLYSURF AL[polyoxyethylene polycyclic phenyl ether phosphoric acid (polyoxyethylene styrenated phenyl ether phosphoric acid); manufactured by DKS Co. Ltd.].

A concentration of the phosphoric acid compound in the method for preserving a leuco chromogen-containing aqueous solution of the present invention is not particularly limited as long as the concentration is capable of preserving the leuco chromogen stably in the aqueous medium, and is usually 0.0001% to 10%, is preferably 0.0005% to 7.5%, and is particularly preferably 0.001% to 5%.

The carboxylic acid compound in the present invention is not particularly limited as long as it is a compound having a carboxyl group ($CO_2H$) or a salt thereof, and examples thereof include polyoxyethylene alkyl ether fatty acid or a salt thereof and N-acylamino acid in which a hydrogen atom of the amino group may be substituted with a substituent and a salt thereof. Examples of the salt include a lithium salt, a sodium salt, a potassium salt, an ammonium salt, a magnesium salt, a calcium salt, and a monoethanolamine salt.

Examples of the fatty acid in the polyoxyethylene alkyl ether fatty acid include acetic acid, propionic acid, and butyric acid. Examples of the alkyl in the polyoxyethylene alkyl ether fatty acid include alkyl having 8 to 20 carbon atoms, and alkyl having 10 to 18 carbon atoms is preferable. Examples of the alkyl having 8 to 20 carbon atoms include octyl, nonyl, decyl, undecyl, dodecyl (lauryl), tridecyl, tetradecyl (myristyl), pentadecyl, hexadecyl (cetyl), heptadecyl, octadecyl (stearyl), oleyl, nonadecyl, and icosyl. Examples of the alkyl having 10 to 18 carbon atoms include decyl, undecyl, dodecyl (lauryl), tridecyl, tetradecyl (myristyl), pentadecyl, hexadecyl (cetyl), heptadecyl, octadecyl (stearyl), and oleyl.

Examples of the substituent in the N-acylamino acid in which a hydrogen atom of the amino group may be substituted with a substituent include an alkyl group, a halogenated alkyl group, and a phenyl group. Examples of the halogenated alkyl group include a fluoroalkyl group, a chloroalkyl group, a bromoalkyl group, and an iodoalkyl group. Examples of the alkyl in the alkyl group and the halogenated alkyl group include alkyl having 1 to 6 carbon atoms. Examples of the alkyl having 1 to 6 carbon atoms include methyl, ethyl, propyl, butyl, pentyl, and hexyl.

Examples of the N-acylamino acid in which a hydrogen atom of the amino group may be substituted with a substituent include N-acylalanine, N-acyl-N-alkylalanine, and N-acyl sarcosine.

Examples of the amino acid include glycine, sarcosine, alanine, β-alanine, valine, leucine, isoleucine, lysine, arginine, serine, threonine, cysteine, methionine, aspartic acid, asparagine, glutamic acid, glutamine, phenylalanine, tyrosine, tryptophan, histidine, and proline, and sarcosine, alanine, and β-alanine are preferable.

Examples of the acyl include acyl having 8 to 20 carbon atoms, and acyl having 10 to 18 carbon atoms is preferable. Examples of the acyl having 8 to 20 carbon atoms include octanoyl, nonanoyl, decanoyl, undecanoyl, dodecanoyl (lauroyl), tridecanoyl, tetradecanoyl, pentadecanoyl, hexadecanoyl (palmitoyl), heptadecanoyl, octadecanoyl (stearoyl), oleoyl, vaccenoyl, linoleoyl, nonadecanoyl, and eicosanoyl. Examples of the acyl having 10 to 18 carbon atoms include decanoyl, undecanoyl, dodecanoyl (lauroyl), tridecanoyl, tetradecanoyl, pentadecanoyl, hexadecanoyl (palmitoyl), heptadecanoyl, octadecanoyl (stearoyl), oleoyl, vaccenoyl, and linoleoyl.

Examples of the alkyl include alkyl having 1 to 6 carbon atoms. Examples of the alkyl having 1 to 6 carbon atoms include methyl, ethyl, propyl, butyl, pentyl, and hexyl.

Specific examples of the carboxylic acid compound include NIKKOL AKYPO RLM 45 NV [polyoxyethylene alkyl ether fatty acid salt (sodium polyoxyethylene lauryl ether acetate); manufactured by Nikko Chemicals Co., Ltd.], NIKKOL AKYPO RLM 45 [polyoxyethylene alkyl ether fatty acid (polyoxyethylene lauryl ether acetic acid); manufactured by Nikko Chemicals Co., Ltd.], NIKKOL AKYPO RLM 100 [polyoxyethylene alkyl ether fatty acid (polyoxyethylene lauryl ether acetic acid); manufactured by Nikko Chemicals Co., Ltd.], NIKKOL ECT-3NEX [polyoxyethylene alkyl ether fatty acid salt (sodium polyoxyethylene tridecyl ether acetate); manufactured by Nikko Chemicals Co., Ltd.], NIKKOL ECTD-3NEX [polyoxyethylene alkyl ether fatty acid salt (sodium polyoxyethylene tridecyl ether acetate); manufactured by Nikko Chemicals Co., Ltd.], NIKKOL ECTD-6NEX [polyoxyethylene alkyl ether fatty acid salt (sodium polyoxyethylene tridecyl ether acetate); manufactured by Nikko Chemicals Co., Ltd.], NEO HITENOL ECL-45 [polyoxyethylene alkyl ether fatty acid salt (sodium polyoxyethylene lauryl ether acetate); manufactured by DKS Co., Ltd.], NIKKOL ALANINATE LN-30 [N-acyl-N-alkylalanine salt (N-lauroyl-N-methyl-β-alanine sodium); manufactured by Nikko Chemicals Co., Ltd.], NIKKOL SARCOSINATE PN [N-acyl sarcosine salt (N-palmitoyl sarcosine sodium); manufactured by Nikko Chemicals Co., Ltd.], NIKKOL SARCOSINATE LN [N-acyl sarcosine salt (sodium N-lauroyl sarcosine); manufactured by Nikko Chemicals Co., Ltd.], NIKKOL SARCOSINATE MN [N-acyl sarcosine salt (N-myristoyl sarcosine sodium); manufactured by Nikko Chemicals Co., Ltd.], and NIKKOL SARCOSINATE OH [N-acyl sarcosine (N-oleoyl sarcosine); manufactured by Nikko Chemicals Co., Ltd.].

A concentration of the carboxylic acid compound in the method for preserving a leuco chromogen-containing aqueous solution of the present invention is not particularly limited as long as the concentration is capable of preserving the leuco chromogen stably in the aqueous medium, and is usually 0.0001% to 10%, is preferably 0.0005% to 7.5%, and is particularly preferably 0.001% to 5%.

The sulfonic acid compound in the present invention is not particularly limited as long as it is a compound having a sulfo group ($SO_3H$) or a salt thereof, and examples thereof include N-acyl taurine or a salt thereof in which a hydrogen atom of the amino group may be substituted with a substituent, α-olefin sulfonic acid or a salt thereof, alkyl sulfocarboxylic acid or a salt thereof, and polyoxyethylene alkyl sulfocarboxylic acid or a salt thereof. Examples of the salt include a lithium salt, a sodium salt, a potassium salt, an ammonium salt, a magnesium salt, a calcium salt, and a monoethanolamine salt.

Examples of the substituent in the N-acyl taurine in which a hydrogen atom of the amino group may be substituted with a substituent include an alkyl group, a halogenated alkyl group, and a phenyl group. Examples of the halogenated alkyl group include a fluoroalkyl group, a chloroalkyl group, a bromoalkyl group, and an iodoalkyl group. Examples of the alkyl in the alkyl group and the halogenated alkyl group include alkyl having 1 to 6 carbon atoms. Examples of the alkyl having 1 to 6 carbon atoms include methyl, ethyl, propyl, butyl, pentyl, and hexyl.

Examples of the N-acyl taurine in which a hydrogen atom of the amino group may be substituted with a substituent include N-acyl taurine and N-acyl-N-alkyl taurine.

Examples of the acyl include acyl having 8 to 20 carbon atoms, and acyl having 10 to 18 carbon atoms is preferable. Examples of the acyl having 8 to 20 carbon atoms include octanoyl, nonanoyl, decanoyl, undecanoyl, dodecanoyl (lauroyl), tridecanoyl, tetradecanoyl, pentadecanoyl, hexadecanoyl (palmitoyl), heptadecanoyl, octadecanoyl (stearoyl), oleoyl, vaccenoyl, linoleoyl, nonadecanoyl, and eicosanoyl. Examples of the acyl having 10 to 18 carbon atoms include decanoyl, undecanoyl, dodecanoyl (lauroyl), tridecanoyl, tetradecanoyl, pentadecanoyl, hexadecanoyl (palmitoyl), heptadecanoyl, octadecanoyl (stearoyl), oleoyl, vaccenoyl, and linoleoyl.

Examples of the alkyl include alkyl having 1 to 6 carbon atoms. Examples of the alkyl having 1 to 6 carbon atoms include methyl, ethyl, propyl, butyl, pentyl, and hexyl.

Examples of the carboxylic acid in the alkyl sulfocarboxylic acid and polyoxyethylene alkyl sulfocarboxylic acid include acetic acid, propionic acid, butyric acid, and succinic acid, and the like can be mentioned. Examples of the alkyl in alkyl sulfocarboxylic acid and polyoxyethylene alkyl sulfocarboxylic acid include alkyl having 8 to 20 carbon atoms, and alkyl having 10 to 18 carbon atoms is preferable. Examples of the alkyl having 8 to 20 carbon atoms include octyl, nonyl, decyl, undecyl, dodecyl (lauryl), tridecyl, tetradecyl (myristyl), pentadecyl, hexadecyl (cetyl), heptadecyl, octadecyl (stearyl), oleyl, nonadecyl, and icosyl. Examples of the alkyl having 10 to 18 carbon atoms include decyl, undecyl, dodecyl (lauryl), tridecyl, tetradecyl (myristyl), pentadecyl, hexadecyl (cetyl), heptadecyl, octadecyl (stearyl), and oleyl.

Specific examples of the sulfonic acid compound include NIKKOL LMT [N-acyl-N-alkyl taurine salt (N-lauroyl-N-methyl taurine sodium); manufactured by Nikko Chemicals Co., Ltd.], NIKKOL PMT [N-acyl-N-alkyl taurine salt (N-palmitoyl-N-methyl taurine sodium); manufactured by Nikko Chemicals Co., Ltd.], NIKKOL MMT [N-acyl-N-alkyl taurine salt (N-myristoyl-N-methyl taurine sodium); manufactured by Nikko Chemicals Co., Ltd.], NIKKOL SMT [N-acyl-N-alkyl taurine salt (N-stearoyl-N-methyl taurine sodium); manufactured by Nikko Chemicals Co., Ltd.]; NIKKOL OS-14 (α-olefin sulfonic acid; manufactured by Nikko Chemicals Co., Ltd.), NIKKOL LSA-F [alkyl sulfocarboxylic acid salt (sodium lauryl sulfoacetate); manufactured by Nikko Chemicals Co., Ltd.]; NEOCOL SW-C [alkyl sulfocarboxylic acid salt (sodium dioctyl sulfosuccinate); manufactured by DKS Co. Ltd.], NEOCOL P [alkyl sulfocarboxylic acid salt (sodium dioctyl sulfosuccinate); manufactured by DKS Co. Ltd.], NEOCOL YSK [alkyl sulfocarboxylic acid salt (sodium dioctyl sulfosuccinate); manufactured by DKS Co. Ltd.], NEO HITENOL L-30 [polyoxyethylene alkyl sulfocarboxylic acid salt (lauryl polyoxyethylene sulfosuccinate disodium); manufactured by DKS Co. Ltd.], NEO HITENOL LS [alkyl sulfocarboxylic acid salt (sodium lauryl sulfosuccinate); manufactured by DKS Co. Ltd.], and NEO HITENOL S-70 [polyoxyethylene alkyl sulfocarboxylic acid salt (alkyl (12 to 14) polyoxyethylene sulfosuccinate·disodium); manufactured by DKS Co. Ltd.].

A concentration of the sulfonic acid compound in the method for preserving a leuco chromogen-containing aqueous solution of the present invention is not particularly limited as long as the concentration is capable of preserving the leuco chromogen stably in the aqueous medium, and is usually 0.0001% to 10%, is preferably 0.0005% to 7.5%, and is particularly preferably 0.001% to 5%.

The sulfuric acid compound in the present invention is not particularly limited as long as it is a compound having a sulfate group ($OSO_3H$) or a salt thereof, and examples thereof include alkyl sulfuric acid or a salt thereof, polyoxyethylene alkyl ether sulfuric acid or a salt thereof, and the like.

Examples of the salt include a lithium salt, a sodium salt, a potassium salt, an ammonium salt, a magnesium salt, a calcium salt, and a monoethanolamine salt.

Examples of the alkyl in alkyl sulfuric acid and polyoxyethylene alkyl ether sulfuric acid include alkyl having 8 to 20 carbon atoms, and alkyl having 10 to 18 carbon atoms is preferable. Examples of the alkyl having 8 to 20 carbon atoms include octyl, nonyl, decyl, undecyl, dodecyl (lauryl), tridecyl, tetradecyl (myristyl), pentadecyl, hexadecyl (cetyl), heptadecyl, octadecyl (stearyl), oleyl, nonadecyl, and icosyl. Examples of the alkyl having 10 to 18 carbon atoms include decyl, undecyl, dodecyl (lauryl), tridecyl, tetradecyl (myristyl), pentadecyl, hexadecyl (cetyl), heptadecyl, octadecyl (stearyl), and oleyl.

Specific examples of the sulfuric acid compound include NIKKOL SLS [alkyl sulfuric acid salt (sodium lauryl sulfate); manufactured by Nikko Chemicals Co., Ltd.] and NIKKOL SBL-2N-27 [polyoxyethylene alkyl ether sulfuric acid salt (sodium polyoxyethylene lauryl ether sulfate); manufactured by Nikko Chemicals Co., Ltd.].

A concentration of the sulfuric acid compound in the method for preserving a leuco chromogen-containing aqueous solution of the present invention is not particularly limited as long as the concentration is capable of preserving the leuco chromogen stably in the aqueous medium, and is usually 0.0001% to 10%, is preferably 0.0005% to 7.5%, and is particularly preferably 0.001% to 5%.

In the method for preserving the leuco chromogen of the present invention, the preservation stability of the leuco chromogen can be evaluated on the basis of coloring of the leuco chromogen-containing aqueous solution, and it can be evaluated that the stronger the coloration is, that is, the larger the absorbance of the leuco chromogen-containing aqueous solution is, the worse the stability is. On the other hand, it can be evaluated that the less the coloring of the leuco chromogen-containing aqueous solution is, that is, the less the absorbance of the leuco chromogen-containing aqueous solution is, the better the stability is.

The leuco chromogen-containing aqueous solution in the present invention refers to an aqueous solution in which the leuco chromogen is dissolved in an aqueous medium, and can be prepared by adding the leuco chromogen to the aqueous medium and dissolving in the aqueous medium.

The aqueous medium in which the leuco chromogen is dissolved is not particularly limited as long as the aqueous medium is capable of dissolving the leuco chromogen, and examples thereof include deionized water, distilled water, and a buffer solution, and a buffer solution is preferable. In preparing the leuco chromogen-containing aqueous solution, an organic solvent can also be used as a solubilization agent for dissolving the leuco chromogen in an aqueous medium. The leuco chromogen-containing aqueous solution can be prepared by adding the leuco chromogen dissolved in the organic solvent to the aqueous medium, and dissolving the leuco chromogen in the aqueous medium.

The organic solvent is not particularly limited as long as the solvent is capable of dissolving the leuco chromogen, and examples thereof include dimethylformamide (DMF), dimethyl sulfoxide (DMSO), dioxane, acetone, methanol, and ethanol.

The pH of the aqueous medium is not particularly limited as long as it is a pH at which the leuco chromogen is dissolved, and is, for example, pH 4 to pH 10. In case of using a buffer solution as an aqueous medium, it is preferable to use a buffer according to the pH to be set. Examples of the buffer used in the buffer solution include a tris (hydroxymethyl)aminomethane buffer, a phosphate buffer, a borate buffer, and a Good's buffer.

Examples of the Good's buffer include 2-morpholinoethanesulfonic acid (MES), bis(2-hydroxyethyl)iminotris(hydroxymethyl)methane (Bis-Tris), N-(2-acetamido)iminodiacetic acid (ADA), piperazine-N,N'-bis(2-ethanesulfonic acid) (PIPES), N-(2-acetamido)-2-aminoethanesulfonic acid (ACES), 3-morpholino-2-hydroxypropanesulfonic acid (MOPSO), N,N-bis(2-hydroxyethyl)-2-aminoethanesulfonic acid (BES), 3-morpholinopropanesulfonic acid (MOPS), N-[tris(hydroxymethyl)methyl]-2-aminoethanesulfonic acid (TES), 2-[4-(2-hydroxyethyl)-1-piperazinyl]ethanesulfonic acid (HEPES), 3-[N,N-bis(2-hydroxyethyl)amino]-2-hydroxypropanesulfonic acid (DIPSO), N-[tris(hydroxymethyl)methyl]-2-hydroxy-3-aminopropanesulfonic acid (TAPSO), piperazine-N,N'-bis(2-hydroxypropanesulfonic acid) (POPSO), 3-[4-(2-hydroxyethyl)-1-piperazinyl]-2-hydroxypropanesulfonic acid (HEPPSO), 3-[4-(2-hydroxyethyl)-1-piperazinyl]propanesulfonic acid [(H) EPPS], N-[tris(hydroxymethyl)methyl]glycine (Tricine), N,N-bis (2-hydroxyethyl)glycine (Bicine), N-tris(hydroxymethyl) methyl-3-aminopropanesulfonic acid (TAPS), N-cyclohexyl-2-aminoethanesulfonic acid (CHES), N-cyclohexyl-3-amino-2-hydroxypropanesulfonic acid (CAPSO), and N-cyclohexyl-3-aminopropanesulfonic acid (CAPS).

The concentration of the buffer solution is not particularly limited as long as the concentration is capable of dissolving the leuco chromogen, and it is usually 0.001 to 2.0 mol/L, and preferably 0.005 to 1.0 mol/L.

Examples of the leuco chromogen in the present invention include a phenothiazine chromogen, a triphenylmethane chromogen, a diphenylamine chromogen, o-phenylenediamine, hydroxypropionic acid, diaminobenzidine and tetramethylbenzidine, and a phenothiazine chromogen is preferable.

Examples of the phenothiazine chromogen include 10-N-carboxymethyl carbamoyl-3,7-bis(dimethylamino)-10H-phenothiazine (CCAP), 10-N-methyl carbamoyl-3,7-bis(dimethylamino)-10H-phenothiazine (MCDP), and 10-N-(carboxymethylaminocarbonyl)-3,7-bis(dimethylamino)-10H-phenothiazine sodium salt (DA-67). Among the phenothiazine chromogens, 10-N-(carboxymethylaminocarbonyl)-3,7-bis(dimethylamino)-10H-phenothiazine sodium salt (DA-67) is particularly preferable.

Examples of triphenylmethane chromogen include N,N,N',N',N",N"-hexa(3-sulfopropyl)-4,4',4"-triaminotriphenylmethane (TPM-PS).

Examples of the diphenylamine chromogen include N-(carboxymethylaminocarbonyl)-4,4'-bis(dimethylamino) diphenylamine sodium salt (DA-64), 4,4'-bis(dimethylamino)diphenylamine, bis[3-bis(4-chlorophenyl)methyl-4-dimethylaminophenyl]amine (BCMA).

A concentration of the leuco chromogen in the leuco chromogen-containing aqueous solution used in the method for preserving the leuco chromogen in the aqueous solution of the present invention is not particularly limited as long as the concentration is capable of dissolving the leuco chromogen in the aqueous medium, and is generally 0.0001 to 2.0 mmol/L, and is preferably 0.0005 to 1.0 mmol/L.

Further, the present invention relates to a method for stabilizing a leuco chromogen in the aqueous solution. The stabilization of the leuco chromogen in the aqueous solution of the present invention means that the leuco chromogen in the leuco chromogen-containing aqueous solution is stabilized against heat, or stabilized against light, and the leuco chromogen in the leuco chromogen-containing aqueous solution is preferably stabilized against the light. Here, stabilization of the leuco chromogen can be evaluated on the basis of coloration, and it can be evaluated that the stronger the coloring of the leuco chromogen-containing aqueous solution is, that is, the larger the absorbance of the leuco chromogen-containing aqueous solution is, the worse the stability is. On the other hand, the less the coloring of the leuco chromogen-containing aqueous solution is, that is, the less the absorbance of the leuco chromogen-containing aqueous solution is, the better the stability is.

In the method for stabilizing leuco chromogen in an aqueous solution of the present invention, at least one acid compound selected from the group consisting of a phosphoric acid compound, a carboxylic acid compound, a sulfonic acid compound, and a sulfuric acid compound are added to a leuco chromogen-containing aqueous solution. Examples of the phosphoric acid compound, the carboxylic acid compound, the sulfonic acid compound, and the sulfuric acid compound which are used in the method for stabilizing leuco chromogen in the aqueous solution of the present invention include the phosphoric acid compound, the carboxylic acid compound, the sulfonic acid compound, and the sulfuric acid compound, which are described above, respectively.

A concentration of the phosphoric acid compound in the method for stabilizing the leuco chromogen in the aqueous solution of the present invention is not particularly limited as long as it is a concentration at which the leuco chromogen is stably preserved in the aqueous medium, and is usually 0.0001% to 10%, is preferably 0.0005% to 7.5%, and is particularly preferably 0.001% to 5%.

A concentration of the carboxylic acid compound in the method for stabilizing the leuco chromogen in the aqueous solution of the present invention is not particularly limited as long as the concentration is capable of preserving the leuco chromogen stably in the aqueous medium, and is usually 0.0001% to 10%, is preferably 0.0005% to 7.5%, and is particularly preferably 0.001% to 5%.

A concentration of the sulfonic acid compound in the method for stabilizing the leuco chromogen in the aqueous solution of the present invention is not particularly limited as long as the concentration is capable of preserving the leuco chromogen stably in the aqueous medium, and is usually 0.0001% to 10%, is preferably 0.0005% to 7.5%, and is particularly preferably 0.001% to 5%.

A concentration of the sulfuric acid compound in the method for stabilizing the leuco chromogen in the aqueous solution of the present invention is not particularly limited as long as the concentration is capable of preserving the leuco chromogen stably in the aqueous medium, and is usually 0.0001% to 10%, is preferably 0.0005% to 7.5%, and is particularly preferably 0.001% to 5%.

Examples of the leuco chromogen and the leuco chromogen-containing aqueous solution used in the method for stabilizing the leuco chromogen in the aqueous solution of the present invention include the leuco chromogen and the leuco chromogen-containing aqueous solution aforementioned in the method for preserving the leuco chromogen, respectively.

A concentration of the leuco chromogen in the leuco chromogen-containing aqueous solution used in the method for stabilizing the leuco chromogen in the aqueous solution of the present invention is not particularly limited as long as the concentration is capable of dissolving the leuco chromogen in the aqueous medium, and the concentration is generally 0.0001 to 2.0 mmol/L, and is preferably 0.0005 to 1.0 mmol/L.

The method for measuring the stability of the leuco chromogen against heat in the aqueous solution of the present invention is not particularly limited as long as it can measure the stability of the leuco chromogen against heat in the aqueous solution, and examples thereof include a method comprising: preserving the aqueous solution containing the leuco chromogen at 20° C. to 40° C. and then measuring the coloring of the aqueous solution with an absorbance meter. The preservation period of the aqueous solution containing the leuco chromogen is not particularly limited as long as the period enables measuring the stability of the leuco chromogen against, and is usually 2 to 7 days.

The method for measuring the stability of the leuco chromogen against light in the aqueous solution of the present invention is not particularly limited as long as it can measure the stability of the leuco chromogen against light in the aqueous solution, and examples thereof include a method comprising: irradiating the aqueous solution containing the leuco chromogen with the light for 4 to 12 hours, measuring the coloring of the aqueous solution after irradiation with an absorbance meter. The intensity of the irradiated light is not particularly limited as long as the intensity enables the measurement of the stability of the leuco chromogen against light, and is usually 500 to 1,500 lux.

(2) Liquid Reagent

The liquid reagent of the present invention is a liquid reagent comprising a leuco chromogen and at least one acid compound selected from the group consisting of a phosphoric acid compound, a carboxylic acid compound, a sulfonic acid compound, and a sulfuric acid compound.

The liquid reagent of the present invention is prepared by adding the leuco chromogen and at least one acid compound selected from the group consisting of a phosphoric acid compound, a carboxylic acid compound, a sulfonic acid compound, and a sulfuric acid compound to an aqueous medium. The liquid reagent may be prepared by adding at least one acid compound selected from the group consisting of a phosphoric acid compound, a carboxylic acid compound, a sulfonic acid compound, and a sulfuric acid compound to a leuco chromogen-containing aqueous solution prepared by adding the leuco chromogen to the aqueous medium, or may be prepared by adding the leuco chromogen to the acid compound-containing aqueous solution prepared by adding at least one acid compound selected from the group consisting of a phosphoric acid compound, a carboxylic acid compound, a sulfonic acid compound, and a sulfuric acid compound to the aqueous medium.

Examples of the leuco chromogen in the liquid reagent of the present invention include the above-described leuco chromogen. Examples of the aqueous medium in the liquid reagent of the present invention include the above-described aqueous medium. Examples of the phosphoric acid compound, the carboxylic acid compound, the sulfonic acid compound, and the sulfuric acid compound in the liquid reagent of the present invention include the phosphoric acid compound, the carboxylic acid compound, the sulfonic acid compound, and the sulfuric acid compound, which are described above, respectively.

The concentration of the phosphoric acid compound, the carboxylic acid compound, the sulfonic acid compound, and the sulfuric acid compound in the liquid reagent of the present invention is usually 0.0001% to 10%, is preferably 0.0005% to 7.5%, and particularly preferably 0.001% to 5%. The concentration of the leuco chromogen in the liquid reagent of the present invention is not particularly limited as long as the concentration enables dissolution of the leuco chromogen in the aqueous medium, and is usually 0.0001 to 2.0 mmol/L, and is preferably 0.0005 to 1.0 mmol/L. In dissolving the leuco chromogen into the aqueous medium, the above-described organic solvent can also be used as a solubilization agent.

EXAMPLES

Hereinafter, the present invention will be described in more detail with reference to examples, but these examples do not limit the scope of the present invention in any way. In this examples and comparative examples, the reagents and enzymes of the following manufacturers were used.

Bis-Tris (manufactured by Dojindo Molecular Technologies, Inc.), peroxidase (manufactured by TOYOBO CO., LTD.), 30% hydrogen peroxide solution (manufactured by Wako Pure Chemical Industries, Ltd.), and bovine serum albumin (BSA, manufactured by PLOMELAIN).

Phosphoric Acid Compound

Sodium phosphate (manufactured by Wako Pure Chemical Industries, Ltd.)

NIKKOL SLP-N [alkyl phosphoric acid salt (sodium lauryl phosphate); manufactured by Nikko Chemicals Co., Ltd.)]

PLYSURF A212C [polyoxyethylene alkyl ether phosphoric acid (polyoxyethylene tridecyl ether phosphoric acid); manufactured by DKS Co. Ltd.]

PLYSURF A215C [polyoxyethylene alkyl ether phosphoric acid (polyoxyethylene tridecyl ether phosphoric acid); manufactured by DKS Co. Ltd.]

PLYSURF A208F [polyoxyethylene alkyl ether phosphoric acid (polyoxyethylene octyl ether phosphoric acid); manufactured by DKS Co. Ltd.]

PLYSURF A219B [polyoxyethylene alkyl ether phosphoric acid (polyoxyethylene lauryl ether phosphoric acid); manufactured by DKS Co. Ltd.]

PLYSURF DB-01 [polyoxyethylene alkyl ether phosphoric acid (polyoxyethylene lauryl ether phosphate·monoethanolamine salt); manufactured by DKS Co. Ltd.]

PLYSURF AL [polyoxyethylene polycyclic phenyl ether phosphoric acid (polyoxyethylene styrenated phenyl ether phosphoric acid); manufactured by DKS Co. Ltd.]

Carboxylic Acid Compound

NIKKOL AKYPO RLM 45 NV [polyoxyethylene alkyl ether fatty acid salt (sodium polyoxyethylene lauryl ether acetate); manufactured by Nikko Chemicals Co., Ltd.]

NIKKOL AKYPO RLM 100 [polyoxyethylene alkyl ether fatty acid salt (sodium polyoxyethylene lauryl ether acetate); manufactured by Nikko Chemicals Co., Ltd.]

NIKKOL ECTD-3NEX [polyoxyethylene alkyl ether fatty acid salt (sodium polyoxyethylene tridecyl ether acetate); manufactured by Nikko Chemicals Co., Ltd.]

NIKKOL ECTD-6NEX [polyoxyethylene alkyl ether fatty acid salt (sodium polyoxyethylene tridecyl ether acetate); manufactured by Nikko Chemicals Co., Ltd.]

NIKKOL ALANINATE LN-30 [N-acyl-N-alkylalanine salt (N-lauroyl-N-methyl-β-alanine sodium); manufactured by Nikko Chemicals Co., Ltd.]

NIKKOL SARCOSINATE PN [N-acyl sarcosine salt (N-palmitoyl sarcosine sodium); manufactured by Nikko Chemicals Co., Ltd.]

NIKKOL SARCOSINATE OH [N-acyl sarcosine salt (N-oleoyl sarcosine); manufactured by Nikko Chemicals Co., Ltd.]

Sulfonic Acid Compound

NIKKOL LMT [N-acyl-N-alkyl taurine salt (N-lauroyl-N-methyl taurine sodium); manufactured by Nikko Chemicals Co., Ltd.]

NIKKOL MMT [N-acyl-N-alkyl taurine salt (N-myristoyl-N-methyl taurine sodium); manufactured by Nikko Chemicals Co., Ltd.]

NIKKOL PMT [N-acyl-N-alkyl taurine salt (N-palmitoyl-N-methyl taurine sodium); manufactured by Nikko Chemicals Co., Ltd.]

NIKKOL SMT [N-acyl-N-alkyl taurine salt (N-stearoyl-N-methyl taurine sodium); manufactured by Nikko Chemicals Co., Ltd.]

NIKKOL OS-14 (α-olefin sulfonic acid; manufactured by Nikko Chemicals Co., Ltd.)

NIKKOL LSA-F [alkyl sulfocarboxylate (sodium lauryl sulfoacetate); manufactured by Nikko Chemicals Co., Ltd.]

NEOCOL SW-C [alkyl sulfocarboxylic acid salt (sodium dioctyl sulfosuccinate); manufactured by DKS Co. Ltd.]

NEOHITENOL L-30 [polyoxyethylene alkyl sulfocarboxylic acid salt (lauryl polyoxyethylene sulfosuccinate·disodium); manufactured by DKS Co. Ltd.]

Sulfuric Acid Compound

NIKKOL SLS [alkyl sulfuric acid salt (sodium lauryl sulfate); manufactured by Nikko Chemicals Co., Ltd.]

NIKKOL SBL-2N-27 [polyoxyethylene alkyl ether sulfuric acid salt (sodium polyoxyethylene lauryl ether sulfate); manufactured by Nikko Chemicals Co., Ltd.]

Example 1

A DA-67-containing aqueous solution having the following composition was prepared.

| Bis-Tris (pH 6.5) | 50 mmol/L |
| DA-67 | 40 μmol/L |

Phosphoric acid compound (refer to Table 1)

Example 2

A DA-67-containing aqueous solution having the following composition was prepared.

| Bis-Tris (pH 6.5) | 50 mmol/L |
| DA-67 | 40 μmol/L |

Carboxylic acid compound (refer to Table 1)

Example 3

A DA-67-containing aqueous solution having the following composition was prepared.

| Bis-Tris (pH 6.5) | 50 mmol/L |
| DA-67 | 40 μmol/L |

Sulfonic acid compound (refer to Table 1)

Example 4

A DA-67-containing aqueous solution having the following composition was prepared.

| Bis-Tris (pH 6.5) | 50 mmol/L |
| DA-67 | 40 μmol/L |

Sulfuric acid compound (refer to Table 1)

Comparative Example 1

A DA-67-containing aqueous solution having the following composition was prepared.

| Bis-Tris (pH 6.5) | 50 mmol/L |
| DA-67 | 40 μmol/L |

Example 5

(1) Preparation of Sample for Evaluation of DA-67 Stability

The aqueous solution containing DA-67 prepared in Example 1 was irradiated with 1,100 lux of light for 10 hours, and the stability of DA-67 against light was evaluated. The aqueous solution containing DA-67 after light irradiation was used as a sample for evaluation of DA-67 stability.

(2) Preparation of Reagent for DA-67 Stability Assay

A reagent for DA-67 stability assay having the following composition was prepared.

<Reagent for DA-67 Stability Assay>

| Bis-Tris (pH 7.0) | 50 mmol/L |
| BSA | 0.005% |

(3) Evaluation for Stability of DA-67 in DA-67-Containing Aqueous Solution

120 μL of reagent for DA-67 stability assay prepared in (2) was added to 30 μL of the freshly-prepared DA-67-containing aqueous solution in Example 1, and the mixture was heated at 37° C. for 5 minutes. Then, the absorbance ($E_{freshly\text{-}prepared}$) of the solution was measured at Hitachi 7170S with a main wavelength of 660 nm and a sub-wavelength of 800 nm. Similar measurement was carried out using the reagent for DA-67 stability assay of (2) instead of the freshly-prepared DA-67-containing aqueous solution to determine the absorbance ($E_{blank}$). $E_{blank}$ was subtracted from $E_{freshly-prepared}$ to determine the absorbance ($\Delta E_{freshly-prepared}$) for the freshly-prepared DA-67-containing aqueous solution.

The absorbance ($\Delta E_{light}$) for the DA-67-containing aqueous solution after light irradiation was calculated by the same method except for using the DA-67-containing aqueous solution after light irradiation (sample for DA-67 stability evaluation) prepared in (1) instead of the freshly-prepared DA-67-containing aqueous solution in Example 1, as a sample. $\Delta E_{freshly-prepared}$ was subtracted from the calculated $\Delta E_{light}$ to determine $\Delta E_1$ as an indicator of the stability of DA-67 against light. The results are shown in Table 1 below. The closer the value of $\Delta E_1$ is to 0, the more suppressed coloring of DA-67 by light irradiation is.

Example 6

$\Delta E_1$ was measured in the same manner as in Example 5 except that the DA-67-containing aqueous solution of Example 2 was used instead of the DA-67-containing aqueous solution of Example 1. The results are shown in Table 1 below.

Example 7

$\Delta E_1$ was measured in the same manner as in Example 5 except that the DA-67-containing aqueous solution of Example 3 was used instead of the DA-67-containing aqueous solution of Example 1. The results are shown in Table 1 below.

Example 8

$\Delta E_1$ was measured in the same manner as in Example 5 except that the DA-67-containing aqueous solution of Example 4 was used instead of the DA-67-containing aqueous solution of Example 1. The results are shown in Table 1 below.

Comparative Example 21

$\Delta E_1$ was measured in the same manner as in Example 5 except that the DA-67-containing aqueous solution of Comparative Example 1 was used instead of the DA-67-containing aqueous solution of Example 1. The results are shown in Table 1 below.

TABLE 1

|  | Compound | | $\Delta E_1$* |
|---|---|---|---|
| Comparative Example 2 | — | | 0.101 |
| Example 5 | Phosphoric acid compound | Sodium phosphate (0.04% = 2.5 mmol/L) | 0.025 |
| Example 5 | Phosphoric acid compound | Sodium phosphate (0.08% = 5 mmol/L) | 0.023 |
| Example 5 | Phosphoric acid compound | Sodium phosphate (0.16% = 10 mmol/L) | 0.052 |
| Example 5 | Phosphoric acid compound | NIKKOL SLP-N (0.05%) | 0.021 |
| Example 5 | Phosphoric acid compound | PLYSURF A212C (0.2%) | 0.052 |
| Example 5 | Phosphoric acid compound | PLYSURF A215C (0.5%) | 0.077 |
| Example 5 | Phosphoric acid compound | PLYSURF A208F (0.5%) | 0.027 |
| Example 5 | Phosphoric acid compound | PLYSURF A219B (0.5%) | 0.064 |
| Example 5 | Phosphoric acid compound | PLYSURF DB-01 (0.5%) | 0.029 |
| Example 5 | Phosphoric acid compound | PLYSURF AL (0.5%) | 0.091 |
| Example 6 | Carboxylic acid compound | NIKKOL AKYPO RLM 45 NV (0.5%) | 0.049 |
| Example 6 | Carboxylic acid compound | NIKKOL AKYPO RLM 100 (0.5%) | 0.063 |
| Example 6 | Carboxylic acid compound | NIKKOL ECTD-3NEX (0.1%) | 0.048 |
| Example 6 | Carboxylic acid compound | NIKKOL ECTD-6NEX (0.5%) | 0.062 |
| Example 6 | Carboxylic acid compound | NIKKOL ALANINATE LN-30 (0.5%) | 0.035 |
| Example 6 | Carboxylic acid compound | NIKKOL SARCOSINATE PN (0.05%) | 0.026 |
| Example 6 | Carboxylic acid compound | NIKKOL SARCOSINATE OH (0.25%) | 0.030 |
| Example 7 | Sulfonic acid compound | NIKKOL LMT (0.1%) | 0.066 |
| Example 7 | Sulfonic acid compound | NIKKOL MMT (0.05%) | 0.053 |
| Example 7 | Sulfonic acid compound | NIKKOL PMT (0.05%) | 0.055 |
| Example 7 | Sulfonic acid compound | NIKKOL SMT (0.025%) | 0.045 |
| Example 7 | Sulfonic acid compound | NIKKOL OS-14 (0.1%) | 0.063 |
| Example 7 | Sulfonic acid compound | NIKKOL LSA-F (0.05%) | 0.046 |
| Example 7 | Sulfonic acid compound | NEOCOL SW-C (0.1%) | 0.055 |
| Example 7 | Sulfonic acid compound | NEO HITENOL L-30 (0.5%) | 0.048 |
| Example 8 | Sulfuric acid compound | NIKKOL SLS (0.05%) | 0.030 |
| Example 8 | Sulfuric acid compound | NIKKOL SBL-2N-27 (0.25%) | 0.042 |

*Change of absorbance after light irradiation for 10 hours

As shown in Table 1, in the DA-67-containing aqueous solution comprising at least one acid compound selected from the group consisting of a phosphoric acid compound, a carboxylic acid compound, a sulfonic acid compound, and a sulfuric acid compound, the coloring by light irradiation was remarkably suppressed as compared with the DA-67-containing aqueous solution which does not comprise any compound of a phosphoric acid compound, a carboxylic acid compound, a sulfonic acid compound, and a sulfuric acid compound. From this result, it was clearly found that DA-67 in the DA-67-containing aqueous solution comprising at least one acid compound selected from the group consisting of a phosphoric acid compound, a carboxylic acid compound, a sulfonic acid compound, and a sulfuric acid compound is stable against light, and the DA-67-containing aqueous solution is stably preserved by at least one acid compound selected from the group consisting of a phosphoric acid compound, a carboxylic acid compound, a sulfonic acid compound, and a sulfuric acid compound, and the DA-67 is stabilized in the aqueous solution by at least one acid compound selected from the group consisting of a phosphoric acid compound, a carboxylic acid compound, a sulfonic acid compound, and a sulfuric acid compound.

INDUSTRIAL APPLICABILITY

The present invention provides a method for preserving a leuco chromogen-containing aqueous solution, a method for stabilizing a leuco chromogen in an aqueous solution, and a liquid reagent comprising a leuco chromogen. The methods and reagent of the present invention are useful for measurement of glycated hemoglobin used for diagnosis of diabetes.

The invention claimed is:

1. A method for preserving a leuco chromogen-containing aqueous solution comprising:
    adding at least one acid compound selected from the group consisting of a first compound, a second compound, a third compound, and a fourth compound to the leuco chromogen-containing aqueous solution,
    wherein the first compound is selected from the group consisting of alkyl phosphoric acid, polyoxyethylene alkyl ether phosphoric acid, polyoxyethylene polycyclic phenyl ether phosphoric acid, and salts thereof,
    wherein the second compound is selected from the group consisting of polyoxyethylene alkyl ether fatty acid, N-acylamino acid in which a hydrogen atom of the amino group may be substituted with a substituent, and salts thereof,
    wherein the third compound is selected from the group consisting of N-acyl taurine in which a hydrogen atom of the amino group may be substituted with a substituent, α-olefin sulfonic acid, alkyl sulfocarboxylic acid, polyoxymethylene alkyl sulfocarboxylic acid, and salts thereof,
    wherein the fourth compound is selected from the group consisting of alkyl sulfuric acid, polyoxyethylene alkyl ether sulfuric acid, and salts thereof, and
    wherein the leuco chromogen comprises a phenothiazine chromogen.

2. The method according to claim 1, wherein the phenothiazine chromogen comprises 10-(carboxymethylaminocarbonyl)-3, 7-bis(dimethylamino)phenothiazine or a salt thereof.

3. A method for stabilizing a leuco chromogen in an aqueous solution comprising:
    adding at least one acid compound selected from the group consisting of a first compound, a second compound, a third compound, and a fourth compound to a leuco chromogen-containing aqueous solution,
    wherein the first compound is selected from the group consisting of alkyl phosphoric acid, polyoxyethylene alkyl ether phosphoric acid, polyoxyethylene polycyclic phenyl ether phosphoric acid, and salts thereof,
    wherein the second compound is selected from the group consisting of polyoxyethylene alkyl ether fatty acid, N-acylamino acid in which a hydrogen atom of the amino group may be substituted with a substituent, and salts thereof,
    wherein the third compound is selected from the group consisting of N-acyl taurine in which a hydrogen atom of the amino group may be substituted with a substituent, α-olefin sulfonic acid, alkyl sulfocarboxylic acid, polyoxymethylene alkyl sulfocarboxylic acid, and salts thereof,
    wherein the fourth compound is selected from the group consisting of alkyl sulfuric acid, polyoxyethylene alkyl ether sulfuric acid, and salts thereof, and
    wherein the leuco chromogen comprises a phenothiazine chromogen.

4. The method according to claim 3, wherein the phenothiazine chromogen comprises 10-(carboxymethylaminocarbonyl)-3, 7-bis(dimethylamino)phenothiazine or a salt thereof.

5. The method according to claim 1, wherein the first compound is selected from the group consisting of sodium lauryl phosphate, polyoxyethylene tridecyl ether phosphoric acid, polyoxyethylene octyl ether phosphoric acid, polyoxyethylene lauryl ether phosphoric acid, polyoxyethylene lauryl ether phosphate-monoethanolamine salt, and polyoxyethylene styrenated phenyl ether phosphoric acid.

6. The method according to claim 1, wherein the second compound is selected from the group consisting of sodium polyoxyethylene lauryl ether acetate, polyoxyethylene lauryl ether acetic acid, sodium polyoxyethylene tridecyl ether acetate, N-lauroyl-N-methyl-β-alanine sodium, N-palmitoyl sarcosine sodium, sodium N-lauroyl sarcosine, N-myristoyl sarcosine sodium, and N-oleoyl sarcosine.

7. The method according to claim 1, wherein the third compound is selected from the group consisting of N-lauroyl-N-methyl taurine sodium, N-palmitoyl-N-methyl taurine sodium, N-myristoyl-N-methyl taurine sodium, N-stearoyl-N-methyl taurine sodium; α-olefin sulfonic acid, sodium lauryl sulfoacetate, sodium dioctyl sulfosuccinate, lauryl polyoxyethylene sulfosuccinate disodium, sodium lauryl sulfosuccinate, and alkyl polyoxyethylene sulfosuccinate disodium.

8. The method according to claim 1, wherein the fourth compound is sodium lauryl sulfate or sodium polyoxyethylene lauryl ether sulfate.

9. The method according to claim 1, wherein the leuco chromogen-containing aqueous solution comprises from 0.0001 mmol/L to 2.0 mmol/L of the leuco chromogen.

10. The method according to claim 3, wherein the first compound is selected from the group consisting of sodium lauryl phosphate, polyoxyethylene tridecyl ether phosphoric acid, polyoxyethylene octyl ether phosphoric acid, polyoxyethylene lauryl ether phosphoric acid, polyoxyethylene lauryl ether phosphate-monoethanolamine salt, and polyoxyethylene styrenated phenyl ether phosphoric acid.

11. The method according to claim 3, wherein the second compound is selected from the group consisting of sodium polyoxyethylene lauryl ether acetate, polyoxyethylene lauryl ether acetic acid, sodium polyoxyethylene tridecyl ether acetate, N-lauroyl-N-methyl-β-alanine sodium, N-palmitoyl sarcosine sodium, sodium N-lauroyl sarcosine, N-myristoyl sarcosine sodium, and N-oleoyl sarcosine.

12. The method according to claim 3, wherein the third compound is selected from the group consisting of N-lauroyl-N-methyl taurine sodium, N-palmitoyl-N-methyl taurine sodium, N-myristoyl-N-methyl taurine sodium, N-stearoyl-N-methyl taurine sodium; α-olefin sulfonic acid, sodium lauryl sulfoacetate, sodium dioctyl sulfosuccinate, lauryl polyoxyethylene sulfosuccinate disodium, sodium lauryl sulfosuccinate, and alkyl polyoxyethylene sulfosuccinate disodium.

13. The method according to claim 3, wherein the fourth compound is sodium lauryl sulfate or sodium polyoxyethylene lauryl ether sulfate.

14. The method according to claim 1, wherein the method comprises adding the first compound to the leuco chromogen-containing aqueous solution.

15. The method according to claim 1, wherein the method comprises adding the second compound to the leuco chromogen-containing aqueous solution.

16. The method according to claim 1, wherein the method comprises adding the third compound to the leuco chromogen-containing aqueous solution.

17. The method according to claim 1, wherein the method comprises adding the fourth compound to the leuco chromogen-containing aqueous solution.

18. The method according to claim 3, wherein the method comprises adding the first compound to the leuco chromogen-containing aqueous solution.

19. The method according to claim 3, wherein the method comprises adding the second compound to the leuco chromogen-containing aqueous solution.

20. The method according to claim 3, wherein the method comprises adding the third compound to the leuco chromogen-containing aqueous solution.

* * * * *